United States Patent [19]

Lynnworth et al.

[11] Patent Number: 4,538,469

[45] Date of Patent: Sep. 3, 1985

[54] INTEGRATED THRESHOLD ARMING METHOD AND APPARATUS

[75] Inventors: Lawrence C. Lynnworth, Waltham; James E. Matson, Brookline, both of Mass.

[73] Assignee: Panametrics, Inc., Waltham, Mass.

[21] Appl. No.: 518,344

[22] Filed: Jul. 29, 1983

[51] Int. Cl.³ ............................................. G01F 1/66
[52] U.S. Cl. .................................. 73/861.27; 73/597
[58] Field of Search ............... 73/597, 861.27–861.29; 367/27, 98, 127; 307/354; 328/150

[56] References Cited

U.S. PATENT DOCUMENTS

| | | | |
|---|---|---|---|
| 3,727,143 | 4/1973 | Garrett | 307/356 X |
| 3,869,915 | 3/1975 | Baumoel . | |
| 3,954,008 | 5/1976 | Yamamoto et al. . | |
| 3,981,191 | 9/1976 | Brown et al. . | |
| 4,022,058 | 5/1977 | Brown . | |
| 4,080,574 | 3/1978 | Loosemore et al. | 73/861.27 X |
| 4,232,548 | 11/1980 | Baumoel . | |

OTHER PUBLICATIONS

Mitsuta, "Sonic Anemometer–Thermometer for Atmospheric Turbulence Measurements", in *Flow, Its Measure and Control in Science and Industry*, Dowdell (Ed.), vol. I, Part I, pp. 341–344, Instrument Society of America, 1974.

Schmidt, "Acoustical Method for Fast Detection and Measurement of Vortices in Wind Tunnels," ICIASF '75 Record, pp. 216–218, 1975.

Crawford et al, "Multipath Artifact Corrections in Ultrasonic Transmission Tomography", *Ultrasonic Imaging*, vol. 4, pp. 234–266, 1982.

"Linear Databook", National Semiconductor Corporation, pp. 9-79-9-84, 1982.

Biber et al, "The Polaroid Ultrasonic Ranging System", Audio Engineering Society, pp. 6–7, 1980.

*Primary Examiner*—Charles A. Ruehl
*Attorney, Agent, or Firm*—Lahive & Cockfield

[57] ABSTRACT

An intervalometer for determining the arrival time of a bandwidth limited energy pulse employs an integrated threshold arming apparatus and method for conditioning an event recognition circuit. The event recognition circuit, which is typically a zero crossing detector, responds to the conditioning signal for detecting a predetermined event after occurrence of said conditioning signal. The integrated threshold arming circuit employs a signal integration circuit responsive preferably to a rectified signal input, and comparison means for determining when the integrated value crosses a predetermined threshold. A dual threshold implementation can also be employed to further discriminate against false noise signals. The apparatus and method are preferably employed in connection with volumetric flow measurements of turbulent and time-varying fluids by ultrasonic pulse interrogation.

17 Claims, 6 Drawing Figures

INTEGRATED THRESHOLD ARMING METHOD AND APPARATUS

The invention relates in general to time measurement apparatus and methods and in particular to a time measurement apparatus and method for accurately determining the arrival of time of a narrow band pulse of energy.

CROSS REFERENCE TO RELATED APPLICATIONS

This application is related to Wallace et al, U.S. application Ser. No. 518,738, filed July 29, 1983, and entitled "Improved Intervalometer Time Measurement Apparatus and Method" and to Smalling et al, U.S. application Ser. No. 518,444, filed July 29, 1983, and entitled "Apparatus and Methods for Measuring Fluid Flow Parameters." To the extent they are not already described in this application, U.S. Ser. Nos. 518,738 and 518,444 are incorporated herein by reference.

BACKGROUND OF THE INVENTION

There exist many fields wherein accurate measurement of a time duration is critical to the success of a system analysis. In many instances, the time interval of measurement is determined by transmitting a relatively short pulse of energy (having a wide bandwidth) and precisely measuring the arrival time duration of the received return pulse. Typically, however, the return pulse is not identical to the transmitted pulse and in many instances the return pulse can be severely affected by the media through which the pulse travels. Typical examples of the use of a measured time interval are the radar and sonar environments wherein the time interval measures distance from the source to an object, for example, an airplane or the sea bottom. Another example of the use of time interval measurement is flow detection and measurement using ultrasonic signal energy, such as that described in Lynnworth, U.S. Pat. No. 3,575,050, issued Apr. 13, 1971, wherein a short pulse of ultrasonic energy is transmitted through a moving fluid in an upstream and a downstream direction. The time intervals of upstream and downstream travel provide measurement data useful in determining fluid flow.

In the ultrasonic flow measurement application in particular, the received pulse often represents the pulse as though it were transmitted through a narrow band filter. In clamp-on flowmeters, for liquids in steel pipe (when the acoustic impedance of the pipe exceeds that of the liquid by more than one order of magnitude), the pipe reverberations cause the received pulse to appear narrowband. At other times, electrical noise-rejection narrowband filters are used to improve the signal-to-noise ratio, and/or the transducers can be quarter-wave impedance matched into low impedance fluids, for example, petrochemical refining flare system headers, yielding a narrowband received signal. In each example, the time extent of the received pulse increases; and therefore, when accurate time durations are required, it is often difficult to exactly measure, consistently, when the pulse is received. In those instances where the time of receipt remains substantially constant from pulse transmittal to pulse transmittal, and/or when the pulse amplitude and shape remain substantially constant from pulse to pulse, relatively standard procedures are available for accurately determining the time when the pulse is received. Thus, for example, a typical approach is to measure the amplitude of the returning pulse; and, when that amplitude exceeds a fixed voltage threshold value, to set the time of receipt as the time of the next zero crossing of the pulse signal. This method is adequate in relatively noise free environments, or where the transmit time is relatively constant from measurement to measurement, and, under those circumstances, produces an accurate "relative" time duration. In the ultrasonic flow measurement system, it is the difference in transit time of the upstream and downstream pulse signals which is important and hence the arrival time, if determined in a consistent manner (even if the time measurement contains a constant error), is adequate for measuring the flow within the pipe.

In many flowmeter instances, however, there is significant noise on the received signal from, for example, interference within the pipe due to either turbulence or pipeline irregularities. In other instances, the transit time varies significantly due to time varying flows and turbulence of the flow. As a result, a typical zero crossing measurement based upon the amplitude threshold method described above, proves inadequate to the task of determining, with a high degree of accuracy, the pulse receive time for a narrow bandwidth pulse signal. In essence, the difficulty is determining the same zero crossing, for example the fifth, for each and every pulse signal received.

It is therefore an object of this invention to accurately measure the time of arrival of a narrow bandwidth pulse signal. Another object of the invention is accurately determining the arrival time of an ultrasonic pulse signal in a volumetric flow measuring environment. Further objects of the invention are a reliable, accurate, easily maintained intervalometer apparatus and method for accurately determining the arrival time of a pulse signal under conditions of varying flow rates and turbulence of the flow. Yet further objects of the invention are an intervalometer method and apparatus which is cost effective to build and easy to manufacture.

SUMMARY OF THE INVENTION

The invention relates to an intervalometer apparatus and method for determining the arrival time of a bandwidth limited energy pulse. The invention features a pulse receiving means responsive to the energy pulse for generating an electrical receive signal representing the undulations of the pulse. An arming circuit responsive to the receive signal generates an arming electrical signal representative of an armed condition. The arming circuit has a signal integrator responsive to the receive signal for generating the arming signal when an integrated value, depending upon the received signal for a single pulse of energy, crosses a preset threshold value. An event recognition circuit responds to the arming signal for detecting an event which occurs in the receive signal during the armed condition. The recognition of the event determines the arrival time of the bandwidth limited pulse.

In preferred embodiments of the invention, the arming circuit has circuitry for electrically rectifying the receive signal for generating a rectified received signal. A signal integrator is thereafter responsive to the rectified received signal for producing the arming signal. The rectification circuit can provide either full wave or half wave rectification. The event being recognized is typically a zero crossing of the received signal at a time when the arming signal corresponds to the armed condition.

The invention is particularly useful in determining the arrival time of a bandwidth limited pulse of ultrasonic energy passing through a fluid medium. This is typically employed, as noted above, in connection with volumetric flow determination in a pipeline. It is characteristic of the pipeline that the received signal, even though the transmitted signal may be relatively wideband, has a relatively narrow bandwidth and hence extends significantly in time relative to the measurement being performed. Therefore, the integrated threshold arming circuitry described hereinabove is employed. In connection with the ultrasonic receiving circuitry, the invention further features a generating circuitry for generating a gating time pulse which substantially provides a window during which, and only during which, integration of the rectified signal can occur.

DESCRIPTION OF THE DRAWINGS

Other objects, features, and advantages of the invention will be apparant to those practiced in the art from the following description taken together with the drawings in which.

DESCRIPTION OF A PREFERRED EMBODIMENT

Figure 1:
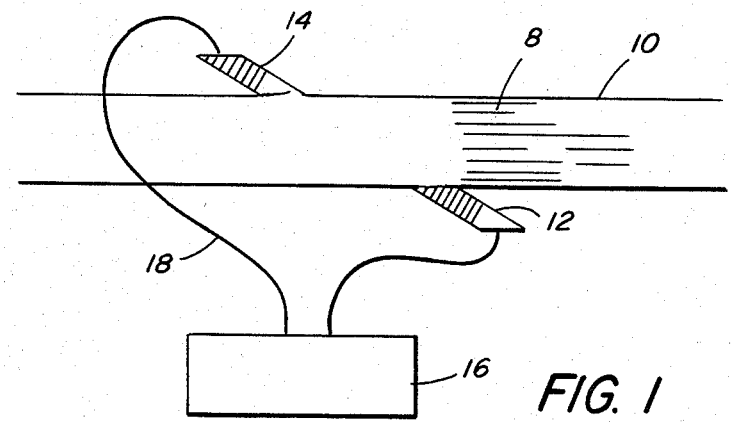
FIG. 1 is a schematic block representation describing a typical application of the inventive apparatus and method.

Referring to FIG. 1, the invention is particularly useful in connection with measuring the volumetric flow of a fluid 8 through a conduit or pipe 10. The fluid can be either a gas or a liquid, can flow in either direction, can have a rapidly varying flow rate, and can be characterized as a laminar flow, a transitional flow, or a turbulent flow. The varying flow rate, flow profile, and fluid composition state conditions will generally affect the time interval between the transmission and reception of a pulse of energy from one transducer, for example a transducer 12, and a second transducer, for example transducer 14. The method and apparatus for using ultrasonic pulses for determining fluid flow is well described in, for example, U.S. Pat. No. 3,575,050 referred to above.

Intervalometer 16 of the present invention is designed to measure, precisely and reliably, the time interval between the transmission of a pulse and its receipt. Typically, the transmitted pulse is a wide band, time limited pulse, such as that illustrated in line (a) of FIG. 2. However, even if the transmitted pulse is a relatively wide band and hence "sharp" pulse, the received pulse often has the appearance of the pulse shown in line (b) of FIG. 2. This pulse has a relatively slowly increasing amplitude, that is, the difference in amplitude from "peak" to "peak" is relatively small. For the pulse shown in FIG. 2, a pulse having a "Q" of about ten, the difference in amplitude of the early cycles from amplitude peak to amplitude peak may be only ten percent. Consequently, small amounts of noise or other interference can easily upset an amplitude threshold arming procedure, after which arming, the first zero crossing determines the time of arrival of the pulse signal. The shape of the pulse in line (b) of FIG. 2 can occur due to resonant effects of the structure of, for example, the pipe walls, the layered media through which the pulse is traveling, or natural resonances in the transducers used for the ultrasonic pulse transmission and reception. Material characteristic resonances can also affect the received signal pulse shape.

In practice, when measuring relatively uniform homogeneous materials, the value of the received amplitude will not vary significantly from moment to moment. Under these circumstances, the conventional and widely-used amplitude threshold method of "arming," followed by a zero crossing detection generally provides quite satisfactory results. On the other hand however, in connection with inhomogeneous solids such as concrete, fiberglass, reinforced plastic, wood, biological specimens, etc., in which the attenuation varies spatially, scanning the media ultrasonically provides a received amplitude which varies temporally, that is, from time moment to time moment, depending upon the region interrogated. Similarly, if an inhomogeneous or turbulent fluid is interrogated ultrasonically, the received amplitude will again vary temporally and, depending upon the nature of the flow, rather unpredictably. In some instances, even changing the direction of interrogation changes the shape and amplitude of the received pulse. (The amplitude change is discussed by Ingard and Singhal in J. Acoustical Society of America, Vol. 60, pp. 1213–1215 (1976), and is based upon laboratory tests in small conduits.) In relatively large conduits typical of a flare stack system in petrochemical refineries, for example especially for high flow rates, the amplitude and phase jitter is quite pronounced and can contain components well above 1 Hz. In such cases, even automatic gain control (AGC) circuits, which are typically used for optimizing the response of the system, cannot prevent some degree of fluctuation in the received amplitude. They can also not prevent a change of pulse shape if conditions vary substantially from one cycle to another.

Accordingly therefore, the usual arming methods which are based solely on the amplitude of the received signal are not sufficiently reliable for the narrow band signal. As noted above, the change of amplitude from one cycle to the next, for a signal having a "Q" of about ten, is not in excess of about ten percent or one dB. Therefore, if jitter in the received signal exceeds one dB, the zero crossing detector will often be falsely armed at the wrong cycle if the conventional amplitude based arming method is used.

According to the invention therefore a different method and apparatus are employed. The basic arming method and apparatus herein disclosed is applicable independent of the number of transducers, and in particular, is applicable for the "pulse-echo" mode of operation where the same transducer functions as both a transmitter and a receiver.

Figure 3:
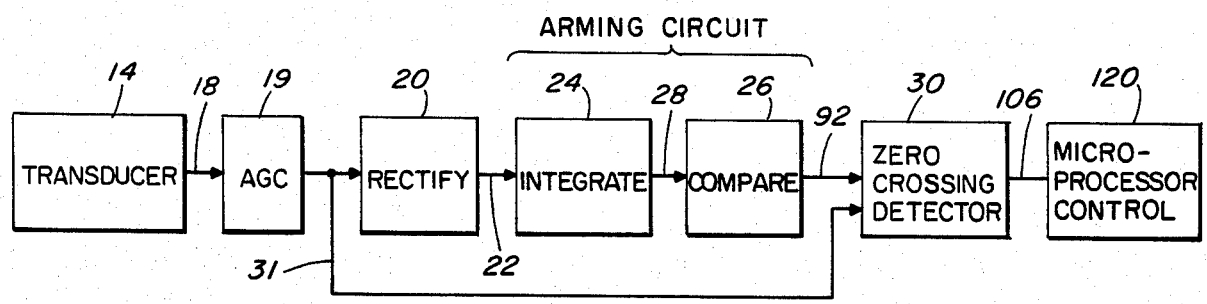
FIG. 3 is an electrical block schematic showing the major components according to the invention.

Referring to FIG. 3, in the illustrated embodiment of the invention, the transducer 14 provides a received output signal over a line 18. The received signal, in the illustrated embodiment, is processed through an automatic gain control circuit 19 and is half wave rectified by a rectification circuit 20. The rectified output over a line 22 is then integrated by an integration circuit 24. A comparison circuit 26 compares the output 28 of the integrator, for each pulse, to a preset threshold value. When the output of the integration crosses the threshold value, the apparatus is then armed and an event detector 30, here shown as a zero crossing detector, detects the next event (here a zero crossing) in the input received signal over a line 31. Rectification may be either full wave or half wave; however, according to the preferred embodiment of the invention, half wave rectification is preferred. The particular arming method and apparatus employed herein is particularly reliable and is substantially insensitive to noise and jitter as described hereinafter.

Figure 2:
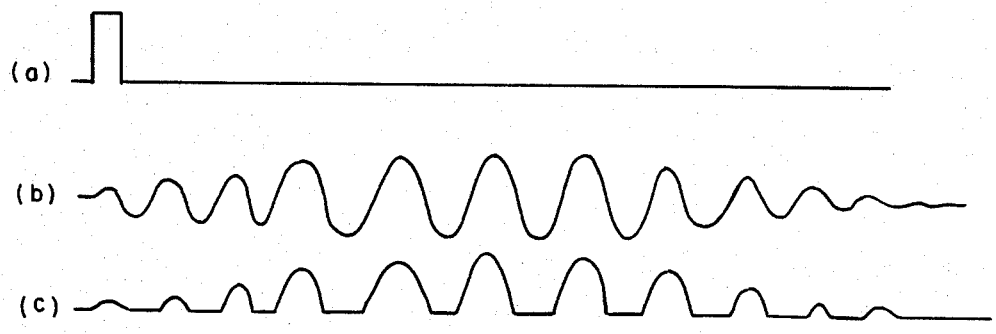
FIG. 2 is a display of transmitted, received, and rectified signals useful in explaining the invention.

According to the integrated threshold arming method and apparatus, and referring to FIG. 2, line (c), the result of rectifying the received signal is a plurality of half-cycle sine waves (approximately) at first increasing in amplitude and then decreasing in amplitude. According to the preferred embodiment, it is the cumulative sum of the areas under, for example, each (positive) half cycle of the received signal which is employed to mark (the arming condition) a zero crossing (or other event) which, in turn, is used to mark (the arming condition) the actual arrival time of the energy pulse.

The integral, I, of an individual half cycle of a sine wave of amplitude A is:

$$I = \int_O^\pi A \sin t\, dt = 2A$$

In other words, the area under each half cycle of a sine wave is simply proportional to the pulse amplitude of the half cycle. With respect to the received and rectified pulse, line (c) of FIG. 2, to the extent that each half cycle or segment is sinusoidal, the area under that segment is proportional to its amplitude. If, then, a sinusoidal signal increases linearly in ten cycles to a maximum amplitude, the relative area contributions of the positive half cycles, starting with the first half cycle, are given approximately by the arithmetic progression 0.2, 0.4, 0.6, . . ., 2.0. If one integrates these contributions, the sum increases as more and more half cycles are added. The results of the first ten half cycles, assuming a linearly increasing amplitude, are shown below:

| Number of half cycles | 1 | 2 | 3 | 4 | 5 | 6 | 7 | 8 | 9 | 10 |
|---|---|---|---|---|---|---|---|---|---|---|
| Relative Amplitude | .1 | .2 | .3 | .4 | .5 | .6 | .7 | .8 | .9 | 1.0 |
| Cumulative Sum | .2 | .6 | 1.2 | 2.0 | 3.0 | 4.2 | 5.6 | 7.2 | 9.0 | 11 |

The contributions and sums would be slightly different for an exponential amplitude or for a different "Q", but the ten cycle linear ramp envelope described above explains the significant advantages of the integrated threshold arming approach.

If the threshold of a comparator 26 (FIG. 3), responsive to the output of the integrator circuitry 24, is set in this example at 2.5, (midway between the sums for the fourth and fifth half cycles), a false arming will occur only if the amplitudes of all of the first four half cycles increase by twentyfive percent, or if the amplitudes of the first five half cycles all decrease by 16.67 percent.

By comparison, considering the progression of half cycle amplitudes, if an amplitude based arming threshold is set to, say 0.45, a false arming will occur if the first four half cycles increase by 12 percent (0.4 to 0.45) or if the first five half cycles decrease by 10 percent (0.5 to 0.45). In this example, the integrated threshold is about twice as tolerant to amplitude fluctuations as the conventional arming based on amplitude alone. Similarly, if it were determined to arm earlier in the pulse, for example when the integral equals 0.8, (to arm on half cycle No. 3), then a false arming will occur if the first two half cycles increase by 34 percent or if the first three half cycles decrease by 34 percent. With amplitude based arming, at a threshold set to 0.25, false arming occurs if all of the half cycles increase or decrease by 20 percent. Again, the integrated threshold arming method is more reliable, that is, more tolerant to amplitude changes (and half-wave rectification is more tolerant to amplitude changes than is full-wave rectification). The integrated threshold thus provides a smoothing effect which translates to improved immunity to attenuation effects which may affect all of the cycles equally. The "smoothing" also provides better immunity to effects whereby only some of the cycles are distorted and to noise spikes which may have a high amplitude but are too brief in time duration to materially affect the integral value. Importantly, high frequency noise and signals which randomly add to some half cycles but subtract from others, tend to be disregarded to the extent that the integration cancels their bipolar contributions.

Figure 4:
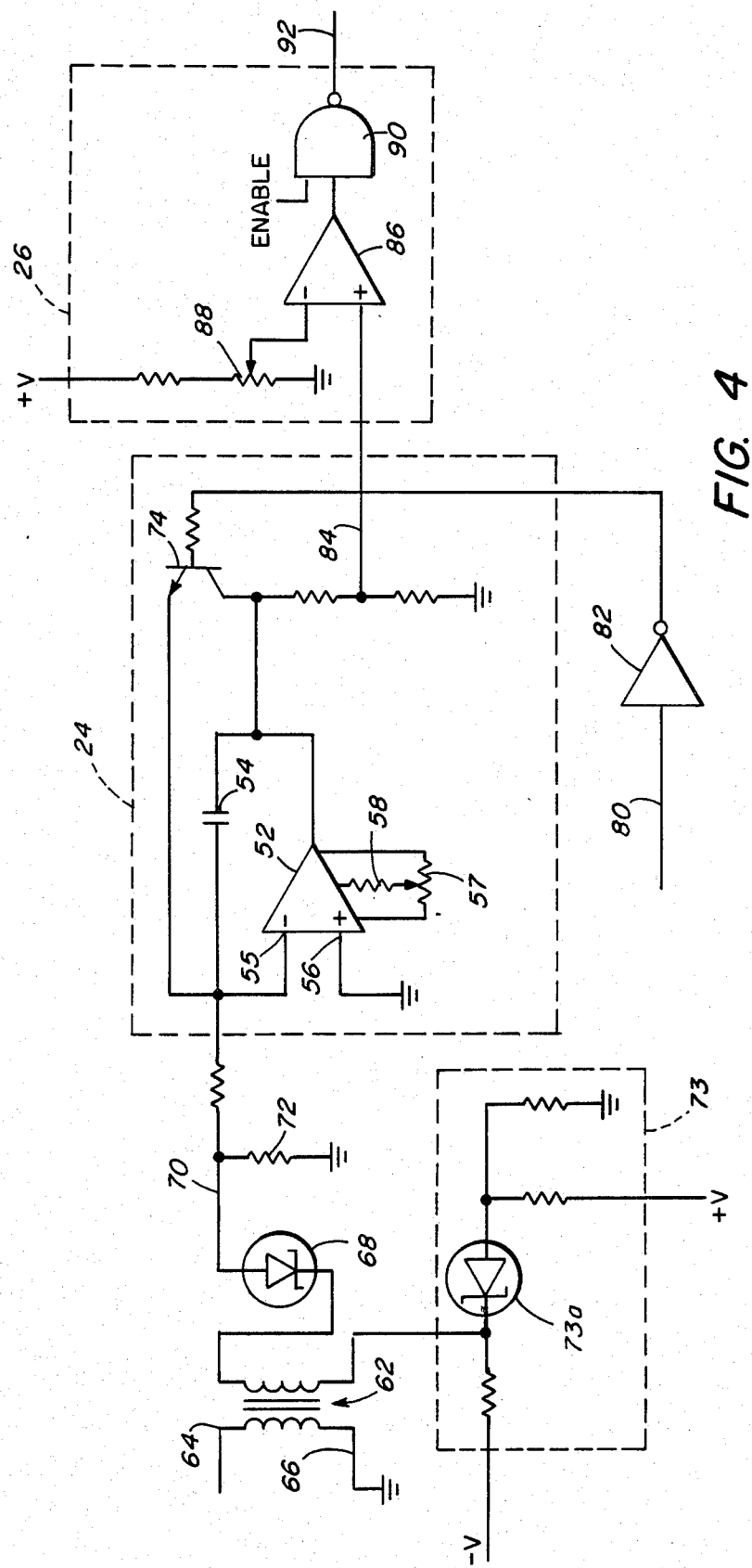
FIGS. 4 and 5 are more detailed electrical schematic diagrams describing a particularly advantageous implementation of the electrical circuitry according to the invention.

Referring now to FIG. 4, in a particularly preferred embodiment of the invention, the integration circuit 24 employs an operational amplifier 52 connected with a capacitor 54 in its feedback circuit connection to a negative amplifier input 55. The positive amplifier input 56 to amplifier 52 is grounded. An offset adjustment employing a potentiometer 57 and a series resistor 58 provides "zeroing" for the amplifier 52.

The input signal to the negative terminal input 55 of operational amplifier 52 is available from the rectification circuit 20. Circuit 20 has a transformer 62 which receives its input across input terminals 64, 66 (terminal 66 being grounded) and provides a rectified output (half wave rectification), from a rectifier 68, over a line 70. A resistor 72 provides a load for a bias network 73 when the amplifier 52 is not in its linear region of operation. Bias network 73 has a rectifying diode 73a which provides temperature compensation for diode 68. Both diodes 68 and 73a are Schottky diodes.

In accordance with the invention, integrator 24 integrates the half cycles of a received pulse signal. To reduce noise problems and to "zero" the output of the integrator at the beginning of a received pulse, the integrator is in a "reset" state until just prior to the expected receipt of the input signal pulse. The reset function is enabled using a transistor 74 having its emitter and collector connected across the capacitor 54. At turn on (i.e. reset), the output of the integrator "ramps down" to about −0.1 volts. This takes approximately 0.1 to 0.2 milliseconds, the time being set by potentiometer 57. The state of transistor 74 is controlled by the signal on its base which, at transistor turn-off, corresponds to a receive window during which a pulse of energy is expected to be available. At transistor 74 turn-off, the integrator 24 integrates the rectified signal on line 70.

Noise immunity is further enhanced by imposition of a deadband, that is, a voltage threshold below which the input signal is not integrated. In the illustrated embodiment, the deadband is provided by the turn-on voltage required for diode 68, typically about 0.4–0.5 volts for a Schottky diode. This voltage is effectively reduced further by bias network 73.

A receive gating signal is available over a line 80. The gating signal is inverted by an inverter 82 and is provided thereby to the transistor 74. The output of the integrator 24 available from a resistor divider, over a line 84, connects to the comparator 26. Comparator 26 employs a comparator integrated circuit 86, having one input connected to the integrator output over line 84 and its other input connected to the output of a potentiometer 88. Potentiometer 88 is connected between a reference voltage and ground. The comparator output is the arming signal and passes through a gating structure 90 and appears over a line 92. This signal changes state when the integrated signal from integrator circuitry 24 crosses the threshold value determined by potentiometer 88.

Figure 5:
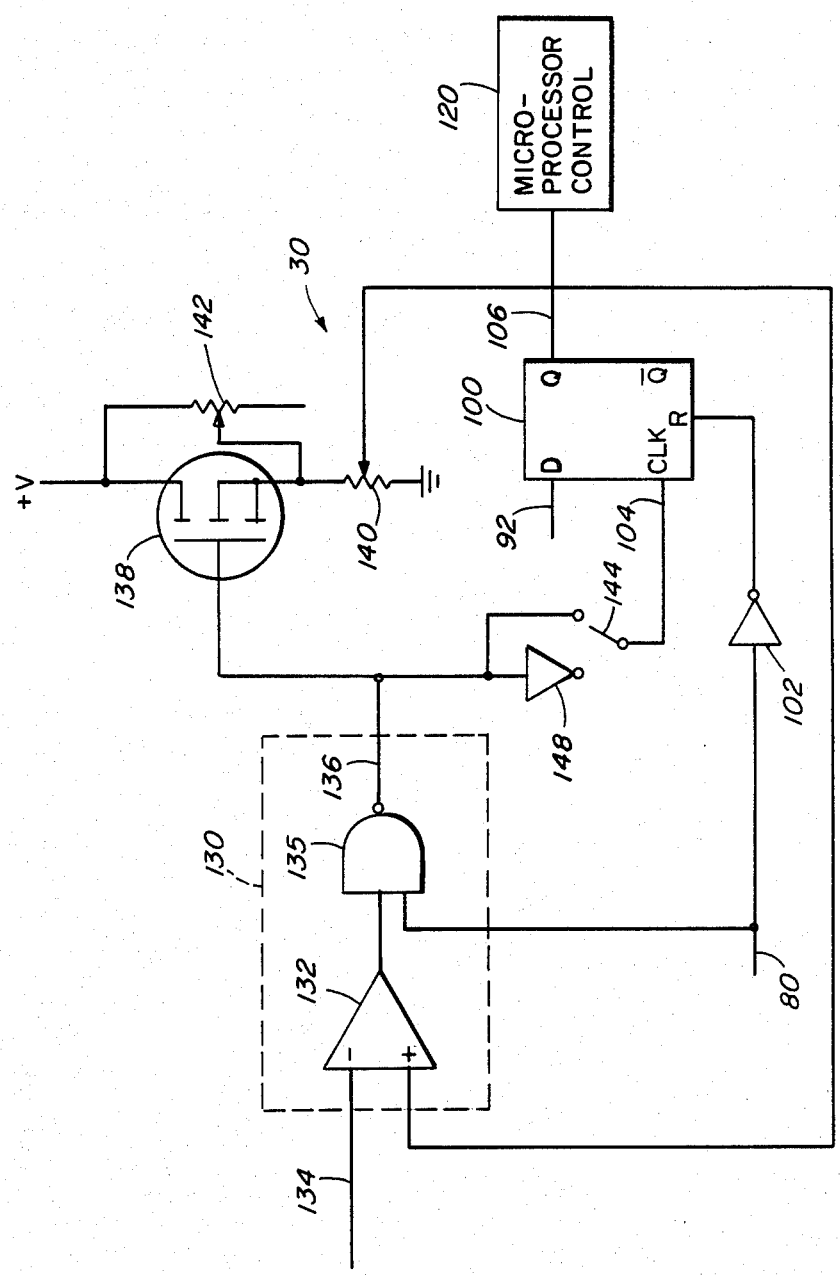

Referring to FIG. 5, the output of the integrated threshold circuitry over line 92, the arming signal, indicates an arming condition when the integrated value crosses the threshold value thereby changing the state of the output signal. This "change of state" enables an event recognition circuit, here the zero-crossing detector 30. Detector 30 employs a flip-flop 100 which, when initially enabled, is in the reset state. Flip-flop 100 has been previously reset by the gating window signal over line 80 (through an inverter 102). When clocked by a signal over a line 104, the flip-flop 100 indicates a zero crossing in the transducer generated receive signal, and that zero crossing signal output of flip-flop 100 over a line 106, is provided to further circuitry including a microprocessor controller 120 to set the time of arrival of the received pulse.

The zero crossing detector 30 further employs a gated comparator 130 having a comparator integrated circuit 132, one side of which receives the electrical pulse receive signal from the transducer over a line 134. A gate 135 is enabled by the gating signal over line 80. The pulse signal over line 134 has been passed through an automatic gain control (AGC) circuitry to provide a substantially constant input signal amplitude level even though changes in the physical media being monitored may occur.

The zero crossing detector employs a varying threshold level to improve zero crossing detection precision. In operation, with no signal present, the output of the zero crossing comparator 130, over a line 136, maintains a MOSFET 138 in an "on" condition. The threshold level is thereby set by an arming level potentiometer 140. In the illustrated embodiment, this quiescent level is a non-zero positive voltage. Thereafter, when a signal pulse is received, comparator 130 changes the state of its output signal when the quiescent threshold is exceeded. This causes the MOSFET 138 to turn off, thereby placing a variable resistor 142 in series with potentiometer 140. The threshold level is thereby effectively lowered, variable resistor 142 having a resistance substantially greater than the resistance of potentiometer 140. Thus, as the input signal approaches zero, going from a positive to a negative voltage (for the position of a switch 144 illustrated in the drawing), the lower threshold crossing is marked by the change of state of the signal on line 136. It is this change of state which acts to clock the flip-flop 100 thereby marking, by a signal over line 106, the first negative going zero crossing occurring after the arming signal over line 92 is received. (In its other position, the switch 144 places an inverter 148 in series with the output of comparator 130 thereby causing detection of a negative to positive voltage at the threshold set by potentiometer 140.)

While the invention has been described with reference to a zero-crossing detector, it will be understood that the actual point to which time is measured at or after arming, can be any of a variety of signal threshold levels. For example, the level at which the arrival time is said to occur can be at any convenient absolute signal level, a selected fraction of the peak signal level, or even at a value greater than a particular cycle's maximum value, for example, at a level fifty percent greater than the peak value of the first cycle following arming. This last alternative can be selected for measuring time at a point where the signal-to-noise ratio is large enough to permit a particularly high accuracy to be obtained.

In this manner, the integrated threshold arming technique accurately, reliably, and repeatedly arms the event recognition detector at the same cycle of each received signal pulse over line 18.

Figure 6:
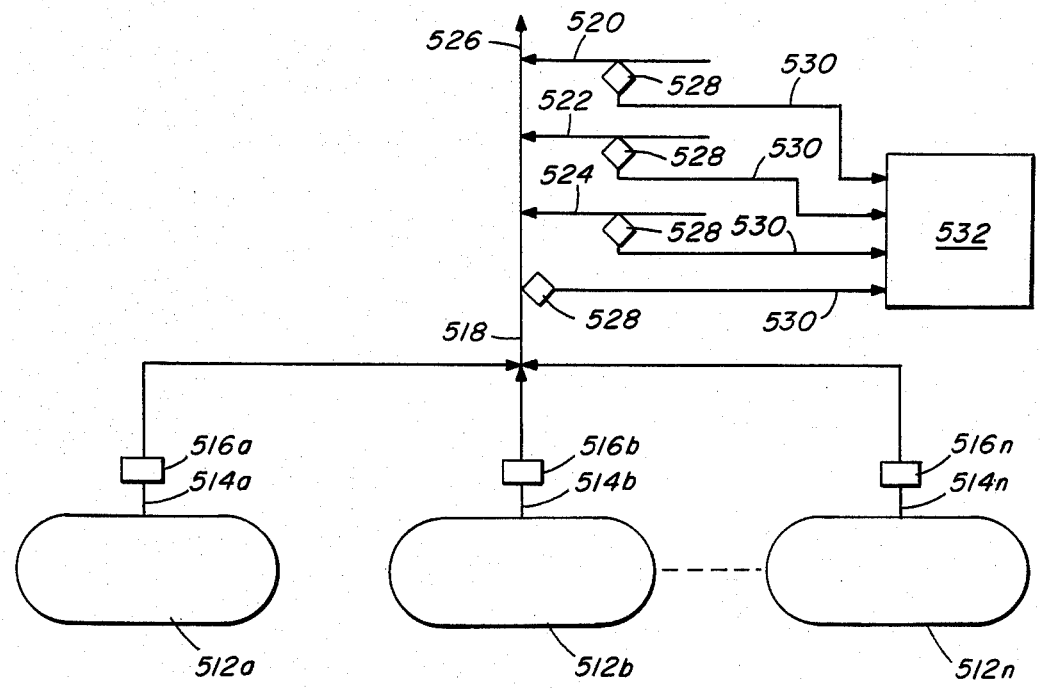
FIG. 6 is a schematic representation of a typical petrochemical application in which the invention is particularly advantageous.

Referring to FIG. 6, in a particular application, the invention can be employed in connection with an intervalometer useful in a petrochemical manufacturing facility. The facility has a plurality of process stations 512a, 512b, . . ., 152n, wherein different manufacturing processes or process stages can be performed. Typically these manufacturing stages are interconnected to form a complete manufacturing process by piping and control connections (not shown). Each of the process stages further includes a single discharge conduit 514a, 514b, . . ., 514n, each having associated therewith a safety valve 516a, 516b, . . ., 516n respectively. The discharges from the stages are collected in a single header 518 which typically has between ten and twenty safety valves and related conduits connected thereto. Further, headers 520, 522, and 524 from other manufacturing stations can be collected into increasingly larger headers until all of the discharges from an entire manufacturing process can be collected into a single large header 526 (the flare stack). The gases from header 526 can be ignited and burned in an elevated flare or burner pit and from there can be safely vented to the environment.

In accordance with this particular application of the invention, the intervalometer is employed to aid in determining the gas flow rate through the headers. Thus, each header can have secured thereto a flow measurement transducer apparatus 528 incorporating, for example, the upstream and downstream transducers. The intervalometer electronics 532 are connected through cables 530 to the transducer elements. The electronics thus include that circuitry illustrated in FIG. 2 which occurs after the transducer 14.

In accordance with this application, one or more of the safety valves 516a, 516b, . . ., 516n can leak and generally the leakage rate is small and of no great concern. At other times, however, the valves can leak excessively for one of many reasons, resulting in a substantial flow through the various headers. The quantity of flow through the headers as well as its content can be important parameters in determining the efficiency of the manufacturing process as well as the safety and efficiency of the flare stack system. The intervalometer herein can be employed for each header or for the flare stack itself to determine the quantity of flow passing therethrough.

Additions, subtractions, deletions and other modifications of the disclosed illustrated embodiment will be within the skill of one practiced in the art and are within the scope of the following claims.

What is claimed is:

1. Intervalometer apparatus for determining the arrival time of a bandwidth limited energy pulse comprising
    pulse receiving means responsive to said pulse for generating an electrical receive signal representing the undulations of the pulse,
    arming means responsive to said receive signal for generating an arming electrical signal representative of an armed condition, said arming means comprising
    a signal integrator responsive to said receive signal for generating said arming signal when an integrated value, dependent upon said receive signal for a said energy pulse, crosses a threshold value, and
    event recognition means responsive to said arming signal and said receiving signal for detecting an event occurring in said receive signal during said armed condition, said event determining the arrival time of said bandwidth limited pulse.

2. The apparatus of claim 1 wherein said arming means further comprises
    means for electrically rectifying said receive signal for generating a rectified received signal and said signal integrator is responsive to said rectified received signal.

3. The apparatus of claim 2 wherein said rectifying means comprises a half-wave rectifier.

4. The apparatus of claim 2 wherein said rectifying means comprises a full-wave rectifier.

5. The apparatus of claim 1 wherein said event recognition means comprises
    means for determining a zero crossing of said receive signal in response to said arming signal representing said armed condition.

6. The intervalometer apparatus of claim 1 further wherein said event recognition means comprises
    a dual threshold crossing detection circuit for detecting a permitted threshold crossing in said receive signal, said dual threshold crossing detection circuit having a first non-zero threshold level for generating an enabled condition, and said threshold crossing circuit detecting a next occurring permitted threshold crossing in said enabled condition, said threshold crossing detection circuit being reset to a deactivated condition after detecting the permitted threshold crossing until said first threshold is next exceeded.

7. The intervalometer apparatus of claim 6 wherein said zero crossing circuit comprises
    a comparator circuit having as one input the electrical receive signal and as another input a threshold level,
    a threshold level generating circuit connected to said another input, for generating said first non-zero threshold level prior to receipt of an energy pulse and for changing the threshold level in response to a receive signal having an amplitude in excess of said non-zero threshold level, said changed threshold being substantially a zero voltage threshold, and
    said threshold level generating circuit returning to said non-zero threshold level upon detection of said permitted threshold crossing.

8. Intervalometer apparatus for determining the arrival time of a bandwidth limited pulse of ultrasonic energy passing through a fluid medium comprising
    pulse transducer receiving means for generating an electrical signal output in response to undulations of the pulse incident thereon,
    integrated threshold arming means comprising
    a rectification circuit for rectifying said transducer electrical signal output, and
    an integration means responsive to said rectification circuit output for generating an arming signal when the integrated value of said rectification circuit output for a pulse crosses a threshold value, and
    threshold crossing recognition means responsive to said arming signal and said transducer electrical signal for detecting a permitted threshold crossing of said transducer electrical signal, said permitted threshold crossing determining the time of arrival of said pulse.

9. The intervalometer apparatus of claim 8 further comprising
    means for generating a gating time pulse for maintaining said integration means in a reset non-integrating condition during a time duration when said ultrasonic pulse should not be received, and for allowing said integration means to integrate said retification circuit output when said ultrasonic pulse should be received.

10. A method for determining the arrival time of a bandwidth limited energy pulse comprising the steps of:
    generating, in response to said pulse, an electrical receive signal representing the undulations of the pulse,
    generating, in response to the receive signal, an arming electrical signal representative of an armed condition, said second generating step comprising the step of integrating the receive signal for generating the arming signal when an integrated value, dependent upon the receive signal, crosses a threshold value, and
    detecting, in response to said arming signal, at a time when said arming signal represents the armed condition, an event occurring in the receive signal during the armed condition, the event determining the arrival time of the bandwidth limited pulse.

11. The method of claim 10 further comprising the step of
    electrically rectifying the receive signal for generating a rectified received signal, and
    integrating said rectified received signal.

12. A method for determining the arrival time of a bandwidth limited energy pulse comprising the steps of:
    generating, in response to said pulse, an electrical receive signal representing the undulations of the pulse,
    electrically rectifying the receive signal for generating a rectified received signal,
    generating, in response to the rectified received signal, an arming electrical signal representative of an armed condition, said second generating step comprising the step of integrating the rectified received signal for generating the arming signal when an integrated value, dependent upon the rectified received signal, crosses a threshold value, and detecting, in response to said arming signal entering said armed condition, a zero-crossing occurring in the receive signal during the armed condition, the zero-crossing determining the arrival time of the bandwidth limited pulse.

13. An interval measuring method for determining the arrival time of a bandwidth limited pulse of ultrasonic energy passing through a fluid medium comprising the steps of generating an electrical received signal output in response to the pulse undulations incident upon a receiving element, rectifying the electrical signal output, integrating said rectified signal, generating an arming signal when the integrated value of the rectified signal for a pulse crosses a threshold value, and detecting, in response to the arming signal, a selected threshold crossing in the electrical signal, said threshold crossing determining the time of arrival of the pulse.

14. The method of claim 13 wherein said integrating step comprises the step of integrating said rectified signal only during a time when said ultrasonic pulse should be received.

15. Intervalometer apparatus for determining the arrival time of a bandwidth limited energy pulse in a flare stack system, comprising a plurality of processing stations, each processing station having associated therewith a safety discharge conduit and a safety discharge valve connected for controlling gaseous discharge from said processing station to said conduit, a header conduit connected to a plurality of said discharge conduits, a first transducer at a first location of said header conduit, a second transducer at a second location of said header conduit, said first and second transducers defining between them an interrogation path, means for measuring an upstream transit time and a downstream transit time for the propagation of said energy pulse between said transducers in an upstream and a downstream direction respectively, said measuring means including means for determining the arrival time of received energy pulses comprising pulse receiving means responsive to each said received pulse for generating an electrical receive signal representing the undulations of the pulse, arming means responsive to said receive signal for generating an arming electrical signal representative of an armed condition, said arming means comprising a signal integrator responsive to said receive signal for generating said arming signal when an integrated value, dependent upon said receive signal for a said energy pulse, crosses a threshold value, and event recognition means responsive to said arming signal and said receive signal for detecting an event occurring in said receive signal during said armed condition, said event determining the arrival time of said bandwidth limited pulse.

16. A method for determining the arrival time of a bandwidth limited pulse in a flare stack system, said flare stack comprising a plurality of processing stations, each processing station having associated therewith a safety discharge conduit and a safety discharge valve connected for controlling discharges from said processing station to said conduit, and a header conduit connected to a plurality of said discharge conduits, said method comprising the steps of exciting a first and a second transducer for emitting acoustic energy therefrom, and measuring an upstream transit time and a downstream transit time for the propagation of a received energy pulse between said transducers in an upstream and a downstream direction respectively, said measuring step determining the arrival time of said pulse and including the steps of generating, in response to said pulse, an electrical receive signal representing the undulations of the received pulses, generating, in response to the receive signal, an arming electrical signal representative of an armed condition, said second generating step comprising the step of integrating the receive signal for generating the arming signal when an integrated value, dependent upon the receive signal, crosses a threshold value, and detecting, in response to said arming signal, an event occurring in the receive signal during the armed condition, the event determining the arrival time of the bandwidth limited pulse.

17. Intervalometer apparatus for determining the arrival time of a bandwidth limited energy pulse of ultrasonic energy comprising pulse receiving means responsive to said pulse for generating an electrical receive signal representing the undulations of the pulse, arming means responsive to said receive signal for generating an arming electrical signal representative of an armed condition, said arming means comprising a signal integrator responsive to said receive signal for generating said arming signal when an integrated value, dependent upon said receive signal for a said energy pulse, crosses a threshold value, said integrator further comprising a deadband threshold circuitry for blocking said receive signal prior to integration when said signal has a value within a predetermined range, and event recognition means responsive to said arming signal and said receive signal for detecting an event occurring in said receive signal during said armed condition, said event determining the arrival time of said bandwidth limited pulse.

* * * * *